(12) United States Patent
Farris

(10) Patent No.: US 7,993,371 B2
(45) Date of Patent: Aug. 9, 2011

(54) SPINAL CONSTRUCT SYSTEM

(75) Inventor: Robert A. Farris, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1228 days.

(21) Appl. No.: 11/118,707

(22) Filed: Apr. 29, 2005

(65) Prior Publication Data
US 2006/0247627 A1 Nov. 2, 2006

(51) Int. Cl.
A61B 17/70 (2006.01)
(52) U.S. Cl. ....................................... 606/246
(58) Field of Classification Search ............... 606/54, 606/60, 61, 69, 70, 71, 105
See application file for complete search history.

(56) References Cited

U.S. PATENT DOCUMENTS

| 4,361,141 | A |   | 11/1982 | Tanner |        |
|-----------|---|---|---------|-----------------|--------|
| 4,771,767 | A |   | 9/1988  | Steffee |        |
| 4,854,304 | A |   | 8/1989  | Zielke |        |
| 5,154,718 | A |   | 10/1992 | Cozad et al. |        |
| 5,217,461 | A |   | 6/1993  | Asher et al. |        |
| 5,330,472 | A |   | 7/1994  | Metz-Stavenhagen |        |
| 5,330,474 | A | * | 7/1994  | Lin | 606/61 |
| 5,336,223 | A |   | 8/1994  | Rogers |        |
| 5,403,314 | A |   | 4/1995  | Currier |        |
| 5,425,732 | A |   | 6/1995  | Ulrich |        |
| 5,486,174 | A |   | 1/1996  | Fournet-Fayard et al. |        |
| 5,498,263 | A | * | 3/1996  | DiNello et al. | 606/61 |
| 5,520,688 | A | * | 5/1996  | Lin | 606/61 |
| 5,562,660 | A |   | 10/1996 | Grob |        |
| 5,575,790 | A |   | 11/1996 | Chen et al. |        |
| 5,593,408 | A |   | 1/1997  | Gayet et al. |        |
| 5,630,816 | A |   | 5/1997  | Kambin |        |
| 5,980,523 | A | * | 11/1999 | Jackson | 606/61 |
| 6,099,528 | A |   | 8/2000  | Saurat |        |
| 6,102,912 | A |   | 8/2000  | Cazin et al. |        |
| 6,106,527 | A | * | 8/2000  | Wu et al. | 606/61 |
| 6,113,600 | A | * | 9/2000  | Drummond et al. | 606/61 |
| 6,264,658 | B1 | * | 7/2001 | Lee et al. | 606/61 |
| 6,328,741 | B1 |   | 12/2001 | Richelsoph |        |
| 6,524,310 | B1 | * | 2/2003 | Lombardo et al. | 606/61 |
| 6,849,076 | B2 | * | 2/2005 | Blunn et al. | 606/105 |
| 2003/0004512 | A1 |   | 1/2003 | Farris et al. |        |
| 2005/0154390 | A1 | * | 7/2005 | Biedermann et al. | 606/61 |
| 2005/0277926 | A1 |   | 12/2005 | Farris |        |

FOREIGN PATENT DOCUMENTS
FR 1 051 847 A1 1/1954
* cited by examiner

Primary Examiner — Nicholas Woodall

(57) ABSTRACT

Embodiments for a spinal construct system including a spinal fixation plate attachable to fixture element in end-to-end fashion with a coupling mechanism that axially and torsionally constrains the first and second rods to one another. In one form, the end-to-end attachment arrangement is aligned along a common axis of the rods. In another form, the axes of the rods are offset laterally relative to one another.

21 Claims, 15 Drawing Sheets

US 7,993,371 B2

SPINAL CONSTRUCT SYSTEM

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments other external stabilization devices have been helpful in the stabilization and fixation of a spinal motion segment, in correcting abnormal curvatures and alignments of the spinal column, and for treatment of other conditions.

While external rod systems have been employed along the vertebrae, the geometric and dimensional features of these rod systems and patient anatomy constrain the surgeon during surgery and prevent optimal placement and attachment along the spinal column. For example, elongated, one-piece rods can be difficult to maneuver into position along the spinal column, and also provide the surgeon with only limited options in sizing and selection of the rod system to be placed during surgery.

SUMMARY

The present invention relates to embodiments for a spinal construct system having a first spinal fixation element attachable to a second spinal fixation element in end-to-end fashion with a coupling mechanism that axially and torsionally constrains the first and second rods to one another. In one embodiment the spinal constructs system includes a spinal fixation plate attachable to fixture element in end-to-end fashion with a coupling mechanism that axially and torsionally constrains the first and second elements to one another. In one form, the end-to-end attachment arrangement is aligned along a common axis of the elements. In another form, the axes of the elements are offset laterally relative to one another.

DETAILED DESCRIPTION

The present invention relates to embodiments for a spinal construct system having a first spinal fixation element attachable to a second spinal fixation element in end-to-end fashion with a coupling mechanism that axially and torsionally constrains the first and second elements to one another.

Figure 1:
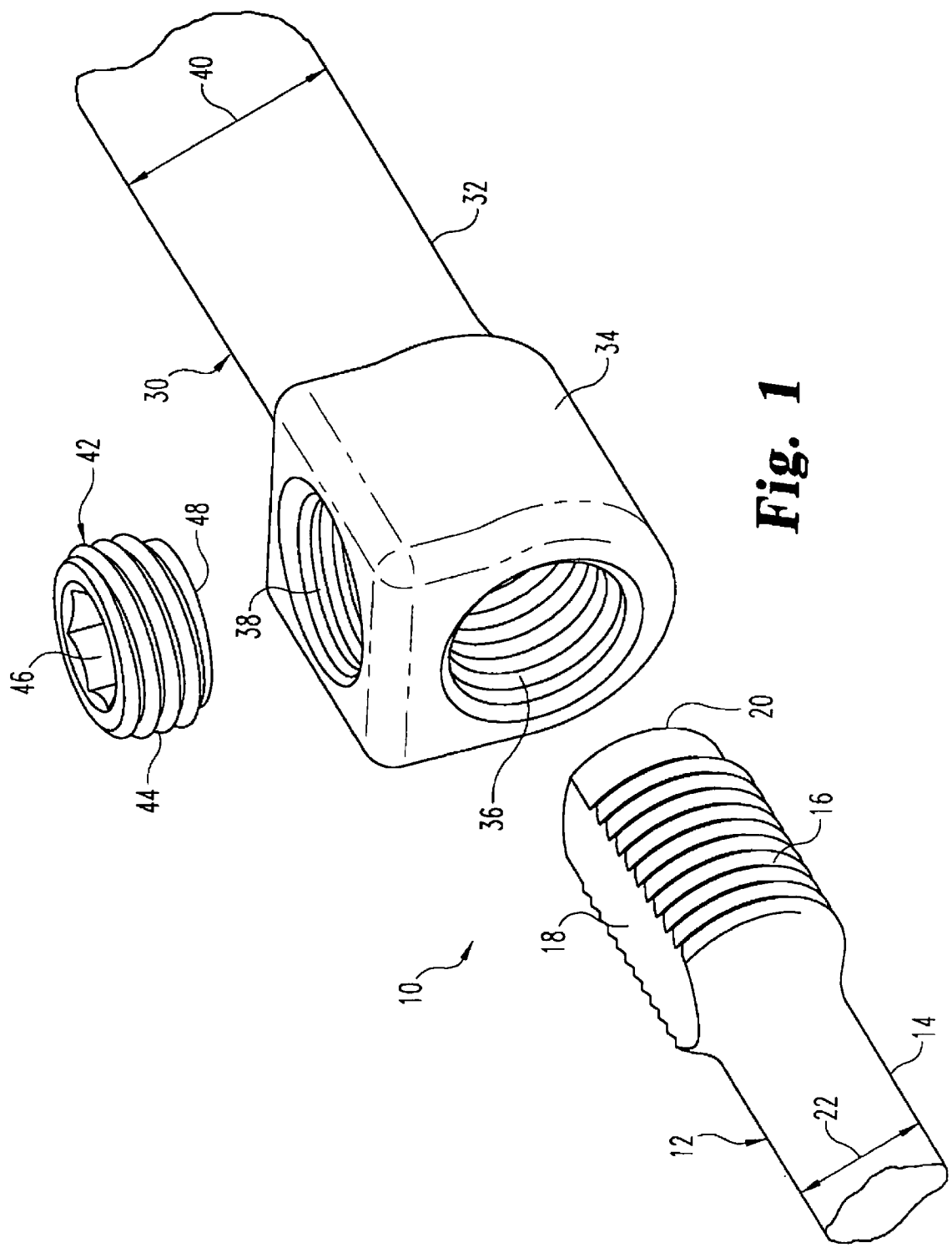
FIG. 1 is an exploded perspective view of a portion of one embodiment spinal construct system.

In FIG. 1 there is shown a spinal construct system 10 including a first rod 12 and a second rod 30. First rod 12 and second rod 30 are releasably coupled to one another in end-to-end fashion with a coupling mechanism 28. Coupling mechanism 28 includes a coupling body on one of the first and second rods 12, 30 and a coupling member on the other of the first and second rods 12, 30. The coupling mechanism 28 is configured to secure rods 12, 30 to one another in end-to-end fashion. This minimizes the footprint or intrusiveness of the coupling mechanism into the tissue surrounding the rod system, and maximizes the length of the rod portion of each rod available for positioning and/or attachment along the spinal column.

Figure 5:
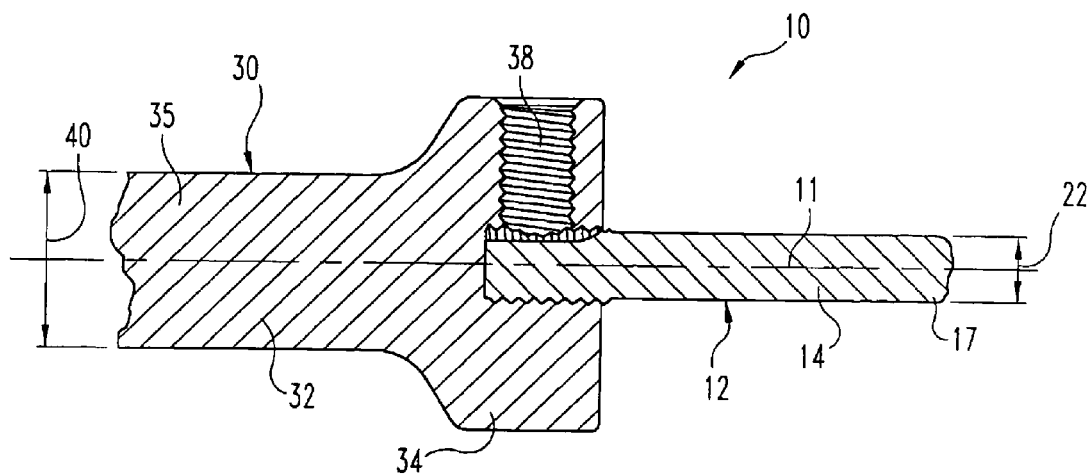
FIG. 5 is a section view of the spinal construct system of FIG. 1 assembled with the engaging member removed from the coupling mechanism.

First rod 12 includes a first rod portion 14 and coupling member 16 at a first end of first rod portion 14. Rod portion 14 extends from coupling member 16 to an opposite second end 17 (FIG. 5.) Second rod 30 includes coupling body 34 at a first end thereof. Rod portion 32 extends from coupling body 34 to an opposite second end 35 (FIG. 5.) One or both of the second ends 17, 35 of rod portions 14, 32 may include a coupling member, a coupling body, or simply provide a terminal end shaped like the corresponding rod portion 14, 32 as shown. In the embodiments illustrated herein, although only one coupling mechanism is shown, one or more of the first and second rods can be adapted for engagement with another rod at each end thereof so that three or more rods may comprise the rod system. The rod portions can be secured to vertebrae of the spinal column system with any one or combination of hooks, screws, bolts, multi-axial screws, staples, cables or wires, sutures, clamps, and/or other attachment devices and systems, with or without interbody fusion devices or implants between vertebrae.

The first rod portion can be provided with a characteristic that differs from a characteristic of the second rod portion. The coupling mechanism allows rods of differing characteristics and rods having the same characteristics to be secured to one another in end-to-end fashion to provide a rod system that is adapted for the anatomy, surgical condition, or surgical procedure. In one embodiment, the characteristic includes a cross-sectional dimension of the rod portions. Other embodiments contemplate selection criteria for selection and assembly of the rod portion to include any one or combination of characteristics, including length, contouring, flexibility, surface features, shape, section modulus, elasticity, materials and material properties, and coatings, for example. For example, in one embodiment a first rod provides a rigid support between a first set of anchors, while the second rod is flexible to provide dynamic stabilization between a second set of anchors. The second rod can be in the form of a tether, cable wire, spring, bumper, or other motion permitting construct.

Figure 2:
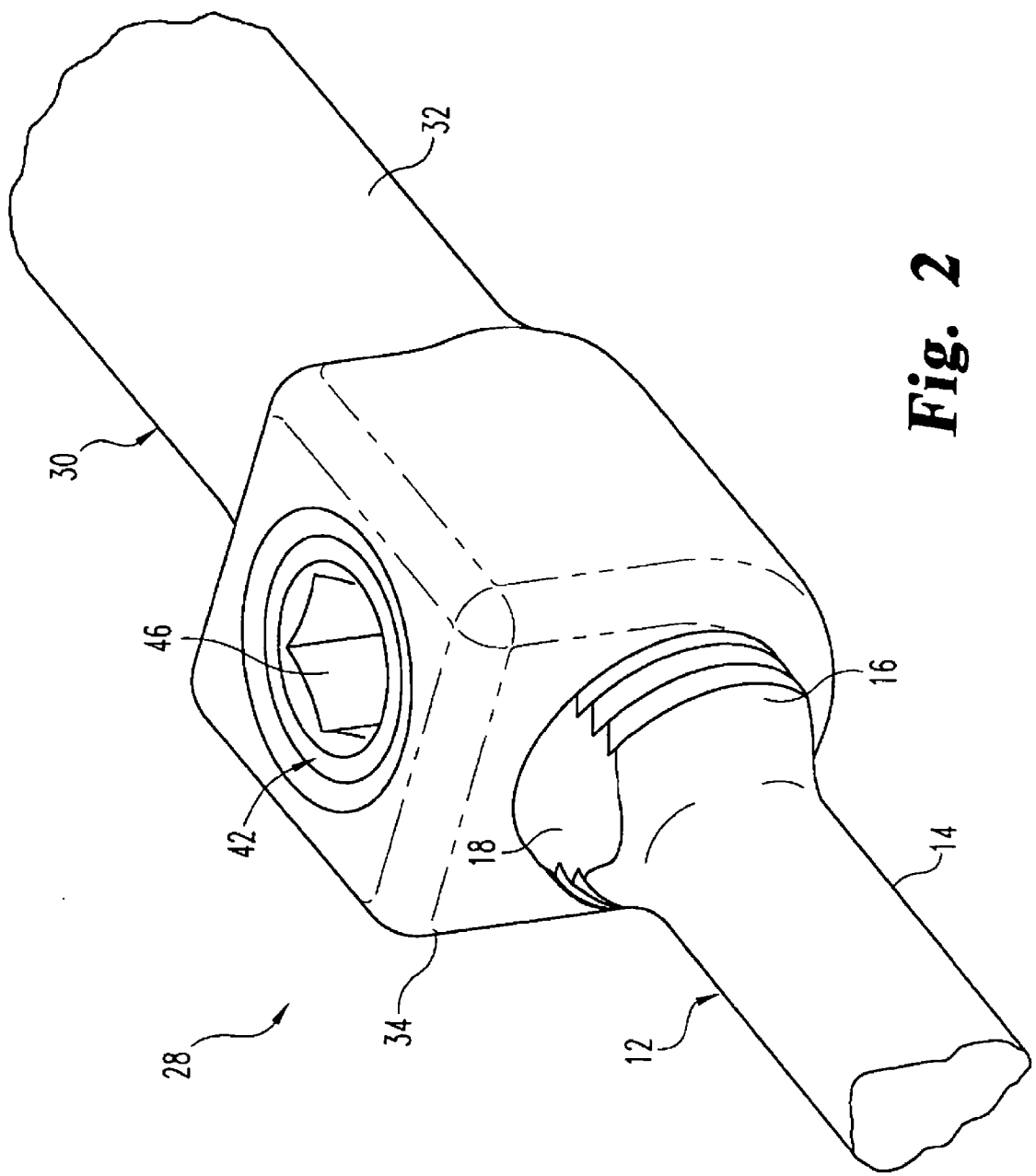
FIG. 2 is a perspective view of the spinal construct system of FIG. 1 assembled.

As shown in FIGS. 1-2 and 5, rod portion 14 extends along longitudinal axis 11 and includes a first cross-sectional dimension 22 between opposite sides thereof transverse to longitudinal axis 11. Similarly, rod portion 32 extends along longitudinal axis 11 and includes a second cross-sectional dimension 40 between opposite sides thereof transverse to longitudinal axis 11. In the illustrated embodiment, cross-sectional dimension 22 corresponds to a diameter of a cylindrical rod portion 14 that is smaller than a diameter corresponding to cross-sectional dimension 40 of a cylindrical rod portion 32. In one specific application, the diameter of first rod portion 14 is sized to extend along a first portion of the spine, such as the cervical region, and the diameter of second rod portion 32 is sized to extend along a second portion of the spine, such as the thoracic region. Other systems contemplate multiple rod portions coupled to one another in end-to-end fashion with characteristics adapted for positioning along any one or combination of the sacral, lumbar, thoracic and cervical regions of the spinal column.

Figure 3:
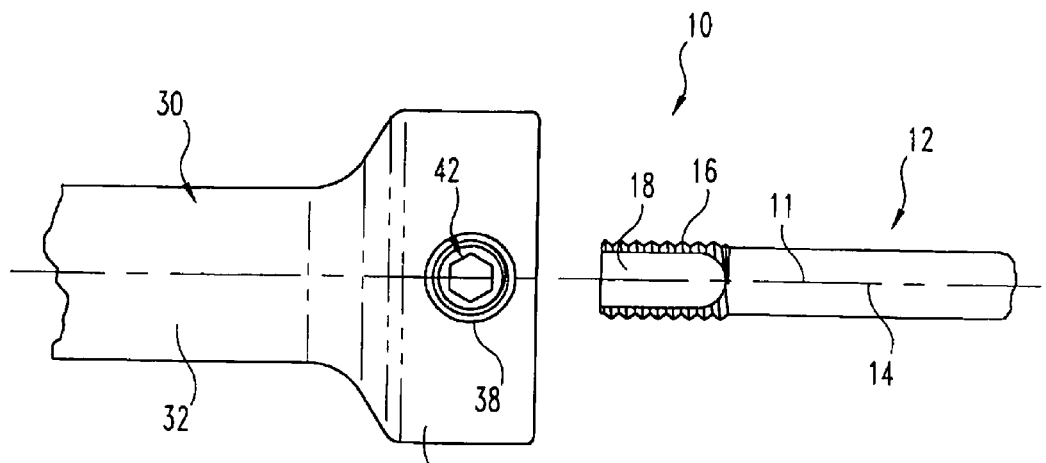
FIG. 3 is an exploded elevational view of the spinal construct system of FIG. 1.
Figure 4:
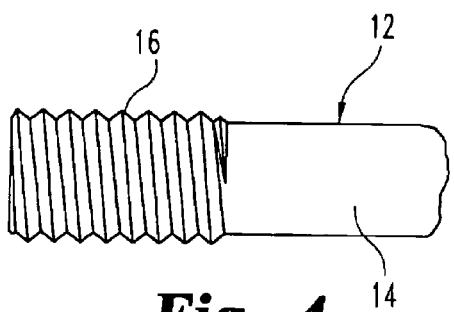
FIG. 4 is a view of a first rod rotated 180 degrees about its longitudinal axis from its FIG. 3 orientation.

Coupling member 16 includes a threaded outer surface extending from rod portion 14 to an end member 20 lacking threads. Coupling member 16 further includes a contact portion 18 along at least one side thereof, as also shown in FIG. 3. Contact portion 18 can be formed by a cutout providing a flat surface extending along coupling member 16. Contact portion 18 can also include a concave surface, a convex surface, a receptacle, or other suitable configuration for contacting an engaging member. As shown in FIG. 5, the thread pattern of coupling member 16 extends completely therearound between the opposite sides of contact portion 18. Other embodiments contemplate that multiple contact portions are provided along coupling member 16 to provide multiple engagement locations for engaging member 42, as discussed further below.

Coupling body 34 can be enlarged relative to rod portion 32 to provide a flange or hub to which coupling member 16 can be releasably engaged. In the illustrated embodiment, coupling body 34 is a cubic block, although other shapes are also contemplated, such as rectangular, cylindrical and non-uniform shapes. Coupling body 34 includes a first bore 36 formed internally therein that extends along and opens along longitudinal axis 11 at an end of coupling body 34. Coupling body 34 further includes a second bore 38 extending therein transversely to first bore 36. As further shown in FIG. 5, second bore 38 can be internally threaded for receipt of an engagement member. Second bore 38 can also be orthogonal to first bore 36, although other orientations are also contemplated.

As shown in FIGS. 2 and 5, rods 12, 30 can be assembled in end-to-end fashion and aligned along longitudinal axis 11 with coupling member 16 received in bore 36 and axially constrained by threaded engagement with coupling body 34. End member 20 facilitates positioning and alignment of coupling member 16 in bore 36, preventing or reducing the possibility of cross-threading coupling member 16 with coupling body 34. The axial load between rods 12, 30 is carried by the engagement between coupling member 16 and coupling body 34, which are also aligned along the axis 11 of rod system 10 when engaged. Accordingly, torsional loading of the components of rod system 10 is minimized since the rods 12, 30 are connected to one another in end-to-end fashion along axis 11. Furthermore, the footprint of coupling mechanism 28 both transversely to rods 12, 30 and along rods 12, 30 is minimized, making the procedure for positioning rod system 10 less invasive, providing additional rod length for contouring and attachment of fasteners for engagement with the spinal column, and minimizing the number of components employed in securing the rods 12, 30 to one another.

Engaging member 42 is positionable in second bore 38 and engageable to coupling member 16 to prevent rod 12 from disengaging from rod 30. In one embodiment, contact portion 18 of coupling member 16 is oriented toward second bore 38, and engaging member 42 is an externally threaded set screw 44 engageable in second bore 38. A tool engaging recess 46 is provided for engagement with a tool, such as a hex driver, to allow the set screw 44 to be driven into second bore 38. Set screw 44 is driven into second bore 38 so that end 48 is in contact with contact portion 18, preventing coupling member 16 from rotating in body 34 and resisting torsional loading between rods 12, 30.

With contact surface 18 aligned with bore 38, the rod portions 14, 32 are oriented in a predetermined alignment with one another determined by the location of contact surface 18 and bore 38 relative to the respective rod portions 14, 32. For example, if one or both of rod portions 14, 32 are provided with non-circular cross-sections, through-holes, or other characteristic along their respective lengths, the characteristics can be oriented relative to contact surface 18 and/or bore 38 so that when contact surface 18 is engaged by engaging member 42, the characteristic of rod portion 14 is positioned in a desired alignment relative rod portion 32. In this manner, the rod portions 14, 32 can be secured with these characteristics in a predetermined alignment relative to one another, and maintained in this alignment by the engagement of engaging member 42 with contact surface 18.

Other embodiments contemplate other arrangements for coupling mechanism 28. For example, engaging member 42 can be a pin that is received in a hole or recess in coupling member 16. Coupling body 34 can be a nut rotatably captured on the end of rod portion 32. Coupling mechanism 28 can include a bayonet locking type device, or a spring-biased ball plunger in coupling member 16 that is received in a detent in coupling body 34.

Figure 6:
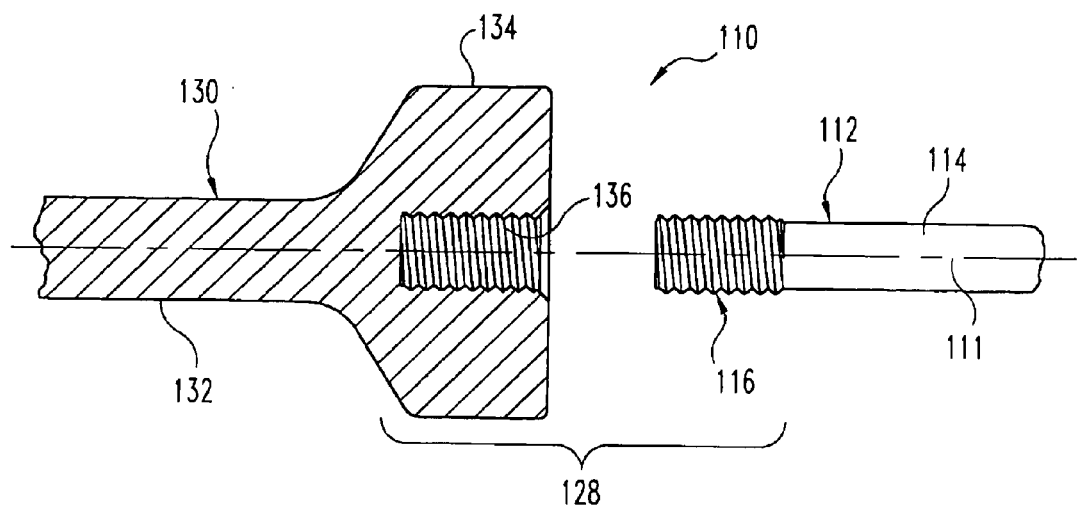
FIG. 6 is an exploded elevation view in partial section of another embodiment spinal construct system.

In FIG. 6, there is shown another embodiment rod system 110 extending along a longitudinal axis 111 and including a first rod 112 having rod portion 114 and coupling member 116. A second rod 130 includes rod portion 132 and a coupling body 134 with an axial bore 136. First and second rod portions 114, 132 can be provided with differing characteristics and axially constrained to one another in end-to-end fashion with a coupling mechanism 128. Body 134 does not include a second bore for an engaging member, and coupling member 116 can be provided completely threaded therearound. To torsionally constrain coupling member 116 in coupling body 134, coupling member 116 can be provided with locking threads to prevent first and second rods 112, 130 from rotating relative to one another. In another embodiment, a simple threaded engagement is provided to axially constrain rods 112, 130 to one another, and relative rotation of rods 112, 130 is resisted by the engagement of rods 112, 130 to the spinal column.

Figure 7:
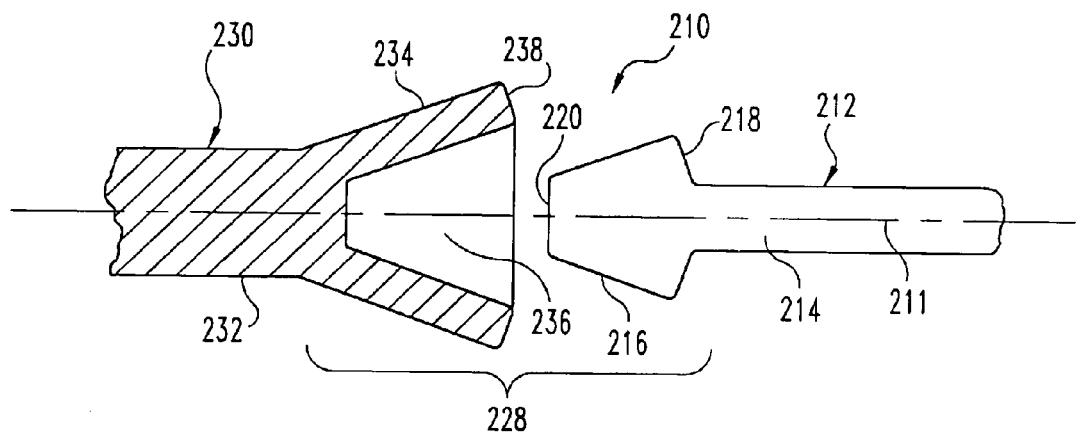
FIG. 7 is an exploded elevation view in partial section of another embodiment spinal construct system.

In FIG. 7, there is shown another embodiment rod system 210 including a first rod 212 and a second rod 230 extending along a longitudinal axis 211. First rod 212 includes a first rod portion 214 and second rod 230 includes a second rod portion 232. First and second rod portions 214, 232 can be provided with differing characteristics and attached to one another in end-to-end fashion with a coupling mechanism 228. First rod 212 includes a coupling member 216 at an end of rod portion 214. Coupling member 216 is externally tapered toward the first end 220 of rod 212, and forms a lip 218 extending about rod portion 214. Coupling body 234 includes an axial bore that is tapered from a first end 238 of second rod 230 toward rod portion 232. Engaging member 216 is press fit into bore 236 so that the tapered outer surface is received in the flared bore to frictionally engage and axially and torsionally constrain first rod 212 to second rod 230 in end-to-end fashion. It is further contemplated that an engaging member can be provided extending between coupling body 234 and coupling member 216 to provide additional fixation in addition to the friction fit between coupling body 234 and coupling member 216.

Figure 8:
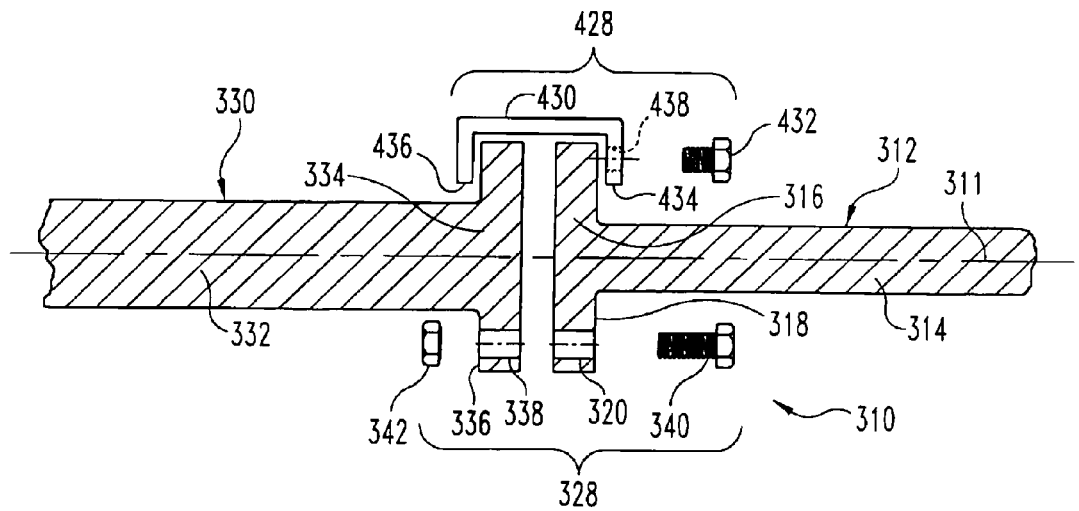
FIG. 8 is an exploded elevation view of another embodiment spinal construct system with two embodiments of a coupling mechanism for coupling the rods to one another.

In FIG. 8, there is shown another embodiment rod system 310 including a first rod 312 and a second rod 330 extending along longitudinal axis 311. First rod 312 includes a first rod portion 314 and second rod 330 includes a second rod portion 332. First rod 312 includes a coupling member at an end of rod portion 314 in the form of a flange or hub 316 extending around first rod portion 314. Flange 316 forms a lip 318 extending about rod portion 314. Second rod 330 includes a coupling body at an end thereof that is also in the form of a flange or hub 334. Flange 334 extends around and forms a lip 336 about second rod portion 332. Flanges 316, 334 are positionable in abutting engagement with one another in end-to-end fashion so that rods 312, 330 having differing characteristics can be secured to one another to provide rod system 310. Coupling mechanism 328 includes a fastener 340 extendable through aligned bores 320, 338 extending parallel to axis 311 through the flanges 316, 334. A nut 342 is engageable with fastener 340 to axially constrain rods 312, 330 together in end-to-end fashion. It is contemplated that a number of fasteners can be positioned about the flanges to provide additional axial constraint and also torsional constraint to rods 312, 330. Although fastener 340 has been shown as a bolt with a nut, other fasteners are also contemplated, including rivets, screws, and bolts threadingly engaged to the flange bores, for example.

Another embodiment coupling mechanism 428 is shown in FIG. 8 that includes a clamping member 430 and an engaging member 432. Clamping member 430 includes arms 434, 436 at opposite ends thereof that extend along adjacent ones of the flanges 316, 334. Fastener 432 extends parallel to axis 311 and is engageable to a bore 438 in arm 434. Fastener 432 is positionable in contact with flange 316 to bias arm 436 into contact with flange 334. Flanges 316, 334 are drawn toward one another to position the flanges in end-to-end contact and axially constrain rods 312, 330 relative to one another. It is contemplated that a number of clamping members can be provided about flanges 316, 334 to provide a secure clamping arrangement to prevent rods 312, 330 from pivoting or splaying relative to one another. It is further contemplated that clamping member 430 can be sized to extend along a portion of the perimeter of flanges 316, 334, and a number of fasteners 432 are provided to clamp first and second rods 312, 330 to one another.

Figure 9:
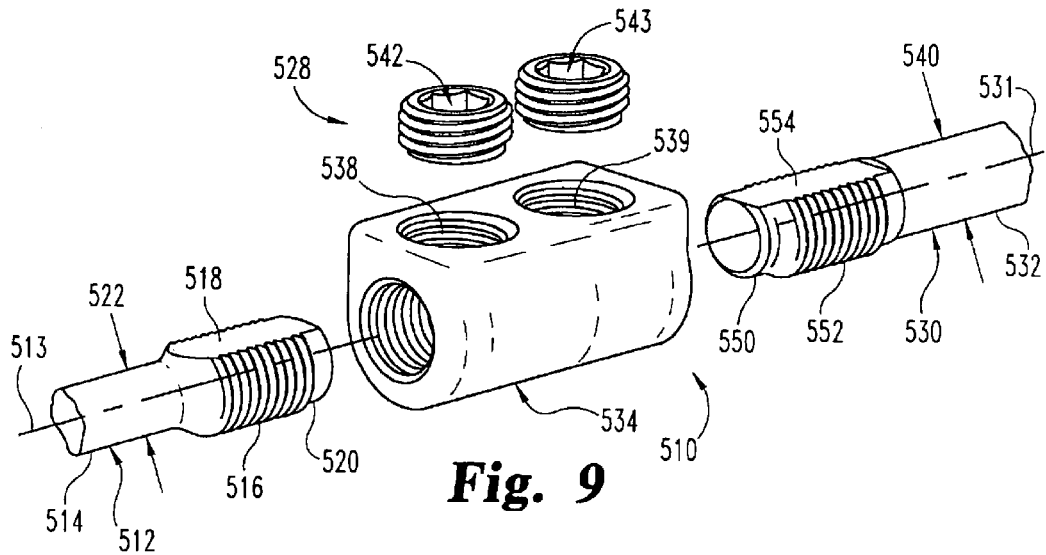
FIG. 9 is an exploded perspective view of a portion of another spinal construct system.
Figure 10:
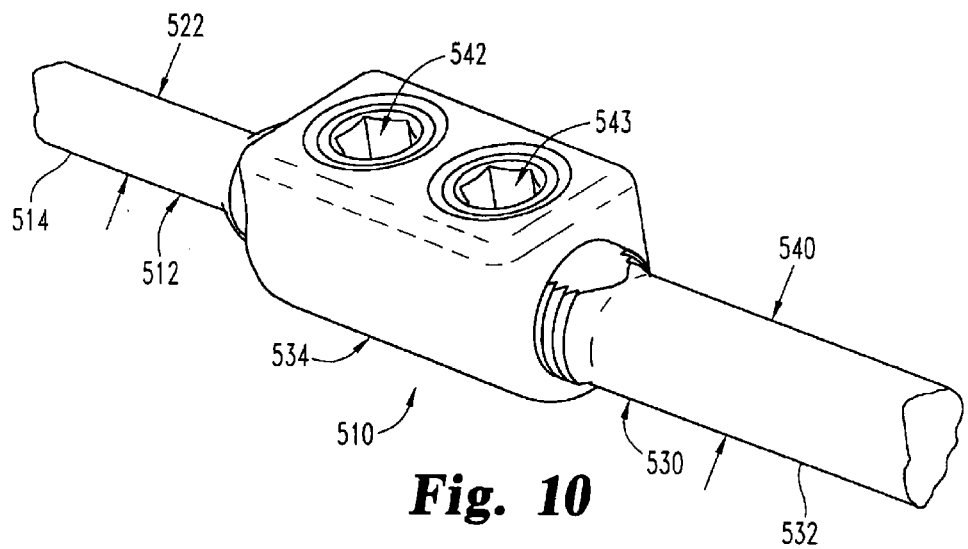
FIG. 10 is an assembled perspective view of the spinal construct system of FIG. 9.

In FIGS. 9-10 there is shown a spinal rod system 510 including a first rod 512 and a second rod 530. First rod 512 and second rod 530 are releasably coupled to one another in end-to-end fashion with a coupling mechanism 528. Coupling mechanism 528 includes a coupling body 534 releasably engageable to each of the first and second rods 512, 530. The coupling mechanism 528 is configured to secure rods 512, 530 to one another in end-to-end fashion while minimizing the footprint or intrusiveness of the coupling mechanism into the tissue surrounding the rod system and maximizing the length of the rod portion of each rod available for positioning and/or attachment along the spinal column.

First rod 512 includes a first rod portion 514 and coupling member 516 at a first end of first rod portion 514. Rod portion 514 extends from coupling member 516 to an opposite second end (not shown.) Second rod 530 includes coupling member 552 at a first end thereof. Rod portion 532 extends from coupling member 516 to an opposite second end (not shown.) One or both of the second ends of rod portions 514, 532 may include a coupling member, a coupling body, or simply provide a terminal end shaped like the corresponding rod portion 514, 532 as shown.

First rod portion 514 can be provided with a characteristic that differs from a characteristic of second rod portion 532. The coupling mechanism 528 allows rods of differing characteristics to be secured to one another in end-to-end fashion to provide a rod system that is adapted for the anatomy, surgical condition, or surgical procedure. In one embodiment, the characteristic includes a cross-sectional dimension of the rod portions 514, 532. Other embodiments contemplate selection criteria for selection and assembly of the rod portion to include any one or combination of characteristics, including length, contouring, flexibility, surface features, shape, section modulus, elasticity, materials and material properties, and coatings, for example.

As shown in FIGS. 9-10, rod portion 514 extends along longitudinal axis 513 and includes a first cross-sectional dimension 522 between opposite sides thereof transverse to longitudinal axis 513. Similarly, rod portion 532 extends along longitudinal axis 531 and includes a second cross-sectional dimension 540 between opposite sides thereof transverse to longitudinal axis 531. In the illustrated embodiment, cross-sectional dimension 522 corresponds to a diameter of a cylindrical rod portion 514 that is smaller than a diameter corresponding to cross-sectional dimension 540 of a cylindrical rod portion 532. In one specific application, the diameter of first rod portion 514 is sized to extend along a first portion of the spine, such as the cervical region, and the diameter of second rod portion 532 is sized to extend along a second portion of the spine, such as the thoracic region. Other systems contemplate multiple rod portions coupled to one another in end-to-end fashion with characteristics adapted for positioning along any one or combination of the sacral, lumbar, thoracic and cervical regions of the spinal column.

Coupling member 516 includes a threaded outer surface extending from rod portion 514 to an end member 520 lacking threads. Coupling member 516 further includes a contact portion 518 along at least one side thereof. Contact portion 518 can be formed by a cutout providing a flat surface extending along coupling member 516. Contact portion 518 can also include a concave surface, a convex surface, a receptacle, or other suitable configuration for contacting an engaging member. The thread pattern of coupling member 516 can extend completely therearound between the opposite sides of contact portion 518. Other embodiments contemplate that multiple contact portions are provided along coupling member 516 to provide multiple engagement locations for engaging member 542, as discussed further below.

Rod 530 similarly includes a coupling member 552 including a threaded outer surface extending from rod portion 532 to an end member 550 lacking threads. Coupling member 552 further includes a contact portion 554 along at least one side thereof. Contact portion 554 can be formed by a cutout providing a flat surface extending along coupling member 552. Contact portion 554 can also include a concave surface, a convex surface, a receptacle, or other suitable configuration for contacting an engaging member. The thread pattern of coupling member 552 can extend completely therearound between the opposite sides of contact portion 554. Other embodiments contemplate that multiple contact portions are provided along coupling member 552 to provide multiple engagement locations for engaging member 543, as discussed further below.

Coupling body 534 can be enlarged relative to rod portions 514, 532 to provide an axial first bore 536 that threadingly receives the respective coupling members 516, 552. In the illustrated embodiment, coupling body 534 is a cubic block, although other shapes are also contemplated, such as rectangular, cylindrical and non-uniform shapes. First bore 536 extends along and opens along longitudinal axes 513, 531 when aligned with the respective rods 512, 530 at opposite ends of coupling body 534. Coupling body 534 further includes a first trans-axial bore 538 and an adjacent second trans-axial bore 539 extending therein transversely to longitudinal axes 513, 531 and in communication with first bore 536. Bores 538, 539 can be internally threaded for receipt of respective ones of the engagement members 542, 543. Bores 538, 539 can be orthogonal to first bore 536, although other orientations are also contemplated.

Rods 512, 530 can be assembled in end-to-end fashion and aligned along longitudinal axes 513, 531 with coupling member 516 received in one end of bore 536 and coupling member 552 received in the opposite end of bore 536. Coupling members 516, 552 are axially constrained by threaded engagement with coupling body 534. End members 520, 550 facilitate positioning and alignment of coupling members 516, 552 in bore 536, preventing or reducing the possibility of cross-threading coupling members 516, 552 with coupling body 534. The axial load between rods 512, 530 is carried by the engagement between coupling members 516, 552 and coupling body 534, which are also aligned along the axes 513, 531 when engaged. Accordingly, torsional loading of the components of rod system 510 is minimized since the rods 512, 530 are connected to one another in end-to-end fashion with axes 513, 531 aligned via coupling mechanism 528. Furthermore, the footprint of coupling mechanism 528 both transversely to rods 512, 530 and along rods 512, 530 is minimized, making the procedure for positioning rod system 510 less invasive, providing additional rod length for contouring and attachment of fasteners for engagement with the spinal column, and minimizing the number of components employed in securing the rods 512, 530 to one another.

Engaging members 542, 543 are positionable in first trans-axial bore 538 and second trans-axial bore 539 and engageable to respective ones of the coupling members 516, 552 to prevent rods 512, 530 from disengaging from coupling body 534. In one embodiment, contact portion 518 of coupling member 516 is oriented toward first trans-axial bore 538, and engaging member 542 is an externally threaded set screw engageable in first trans-axial bore 538. Engaging member 542 is driven into first trans-axial bore 538 so that it is in contact with contact portion 518, preventing coupling member 516 from rotating in coupling body 534 and resisting torsional loading of rod 512. Similarly, contact portion 554 of coupling member 552 is oriented toward second bore 539, and engaging member 543 is an externally threaded set screw engageable in second trans-axial bore 539. Engaging member 542 is driven into bore 539 so that it is in contact with contact portion 554, preventing coupling member 552 from rotating in coupling body 534 and resisting torsional loading of rod 530.

With contact surface 518 aligned with bore 538, the rod portion 514 is oriented in a predetermined alignment determined by the location of contact surface 518 and bore 538 relative to the respective rod portion 514. Similarly, with contact surface 554 aligned with bore 539, the rod portion 532 is oriented in a predetermined alignment determined by the location of contact surface 554 and bore 539 relative to the respective rod portion 532. For example, if one or both of rod portions 514, 532 are provided with non-circular cross-sections, through-holes, or other characteristic along their respective lengths, the characteristics can be oriented relative to contact surface 518, 554 and/or bores 538, 539 so that engagement by the respective engaging members 542, 543 provides a desired alignment. The rod portions 514, 532 can be secured with these characteristics in a predetermined alignment relative to one another, and maintained in this alignment by the engagement of engaging members 542, 543 with contact surfaces 518, 554.

Figure 11:
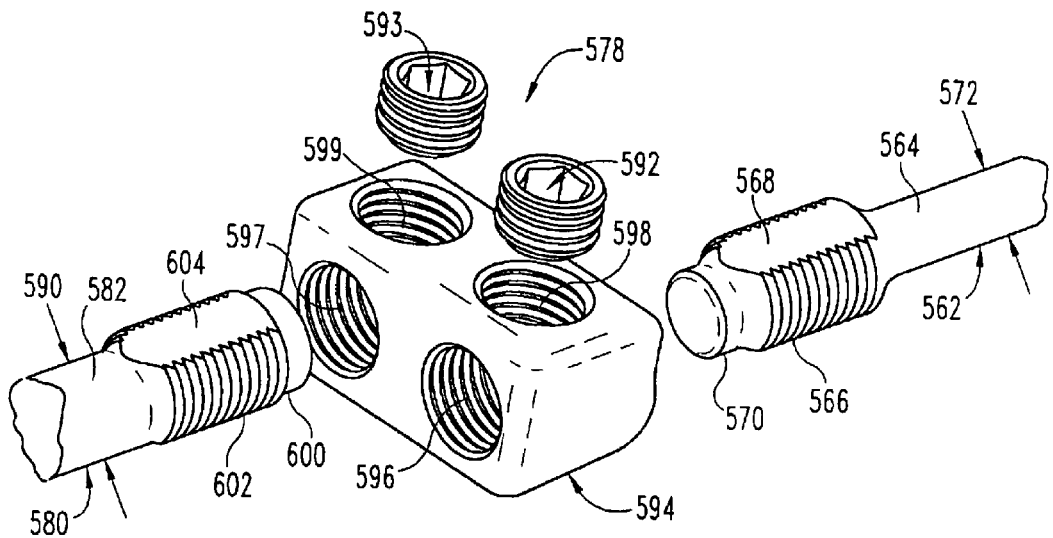
FIG. 11 is an exploded perspective view of a portion of another spinal construct system.
Figure 12:
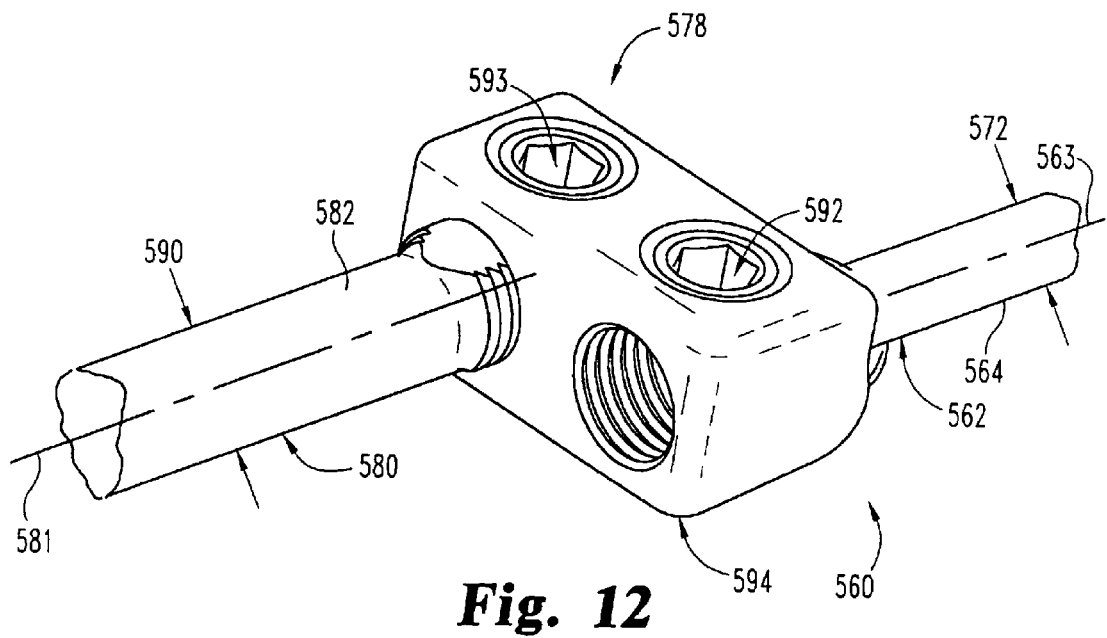
FIG. 12 is an assembled perspective view of the spinal construct system of FIG. 11.

Referring to FIGS. 11 and 12, there is shown another embodiment a spinal rod system 560 including a first rod 562 and a second rod 580. First rod 562 and second rod 580 are releasably coupled to one another in end-to-end fashion with a coupling mechanism 578.

Coupling mechanism 578 includes a coupling body 594 releasably engageable to each of the first and second rods 562, 580. The coupling mechanism 578 is configured to secure rods 562, 530 to one another in end-to-end fashion with their longitudinal axes 563, 581 laterally offset from one another. This allows the relative positioning of rods 562, 580 to be offset as may be desirable to accommodate the spinal anatomy while minimizing the footprint or intrusiveness of the coupling mechanism into the tissue surrounding the rod system, and maximizing the length of the rod portion of each rod available for positioning and/or attachment along the spinal column.

Like rods 512, 530 discussed above, first rod 562 includes a first rod portion 564 and coupling member 566 at a first end of first rod portion 564. Rod portion 564 extends from coupling member 566 to an opposite second end (not shown.) Second rod 580 includes coupling member 602 at a first end thereof. Rod portion 582 extends from coupling member 602 to an opposite second end (not shown.) Rod portions 564, 582 can be provided with characteristics that differ from one another.

As shown in FIGS. 11-12, rod portion 564 extends along longitudinal axis 563 and includes a first cross-sectional dimension 572 between opposite sides thereof transverse to longitudinal axis 563. Similarly, rod portion 582 extends along longitudinal axis 581 and includes a second cross-sectional dimension 590 between opposite sides thereof transverse to longitudinal axis 581. In the illustrated embodiment, cross-sectional dimension 572 corresponds to a diameter of a cylindrical rod portion 564 that is smaller than a diameter corresponding to cross-sectional dimension 590 of a cylindrical rod portion 582. In still other embodiments, the diameters of the rod portions 582, 564 are the same.

Coupling member 566 includes a threaded outer surface extending from rod portion 564 to an end member 570 lacking threads. Coupling member 566 further includes a contact portion 568 along at least one side thereof. Contact portion 568 can be formed by a cutout providing a flat surface extending along coupling member 566. Contact portion 568 can also include a concave surface, a convex surface, a receptacle, or other suitable configuration for contacting an engaging member. The thread pattern of coupling member 566 can extend completely therearound between the opposite sides of contact portion 568.

Other embodiments contemplate that multiple contact portions are provided along coupling member 566 to provide multiple engagement locations for engaging member 592, as discussed further below.

Rod 580 similarly includes a coupling member 602 including a threaded outer surface extending from rod portion 582 to an end member 600 lacking threads. Coupling member 602 further includes a contact portion 604 along at least one side thereof. Contact portion 604 can be formed by a cutout providing a flat surface extending along coupling member 602. Contact portion 604 can also include a concave surface, a convex surface, a receptacle, or other suitable configuration for contacting an engaging member. The thread pattern of coupling member 602 can extend completely therearound between the opposite sides of contact portion 604. Other embodiments contemplate that multiple contact portions are provided along coupling member 602 to provide multiple engagement locations for engaging member 593, as discussed further below.

Coupling body 594 can be enlarged relative to rod portions 564, 582 to provide an axial first bore 596 that threadingly receives coupling member 566, and an axial second bore 597 offset laterally from and extending parallel to first bore 596 to threadingly receive coupling member 602. In the illustrated embodiment, coupling body 594 is a rectangular block, although other shapes are also contemplated, such as cubic, cylindrical and non-uniform shapes.

First bore 596 extends along and opens on longitudinal axis 563 when aligned with rod 562, and second bore 597 extends along and opens on longitudinal axis 581 when aligned with rod 580. Coupling body 594 further includes a first trans-axial bore 598 and an adjacent second trans-axial bore 599 extending therein transversely to respective ones of the longitudinal axes 563, 581 and in communication with respective ones of the bores 596, 597. Bores 598, 599 can be internally threaded for receipt of respective ones of the engagement members 592, 593. Bores 598, 599 can be orthogonal to the respective bores 596, 597, although other orientations are also contemplated.

Rods 562, 580 can be assembled in end-to-end fashion with coupling member 566 received in first bore 596 and coupling member 602 received in second bore 597. Coupling members 566, 602 are axially constrained by threaded engagement with coupling body 594. End members 570, 600 facilitate positioning and alignment of coupling members 566, 602 in bores 596, 597, preventing or reducing the possibility of cross-threading coupling members 566, 602 with coupling body 594. The axial load between rods 562, 580 is carried by the engagement between coupling members 566, 602 and coupling body 594.

The axial restraint provided by the threaded engagement of rods 562, 580 to coupling body 594 allows the length of coupling body 594 along axes 563, 581 to be minimized, thus minimizing its intrusion into the adjacent anatomy and maximizing the rod length available for attachment of connection elements. The lateral offset provided by coupling mechanism 578 allows application of rods 562, 580 in anatomical locations where alignment of axes 563, 581 would not be optimal. Engaging members 592, 593 are positionable in first trans-axial bore 598 and second trans-axial bore 599, respectively, and engageable to respective ones of the coupling members 566, 602 to contact the aligned contact portions 568, 604 to prevent rods 562, 580 from disengaging from coupling body 594.

Figure 13:
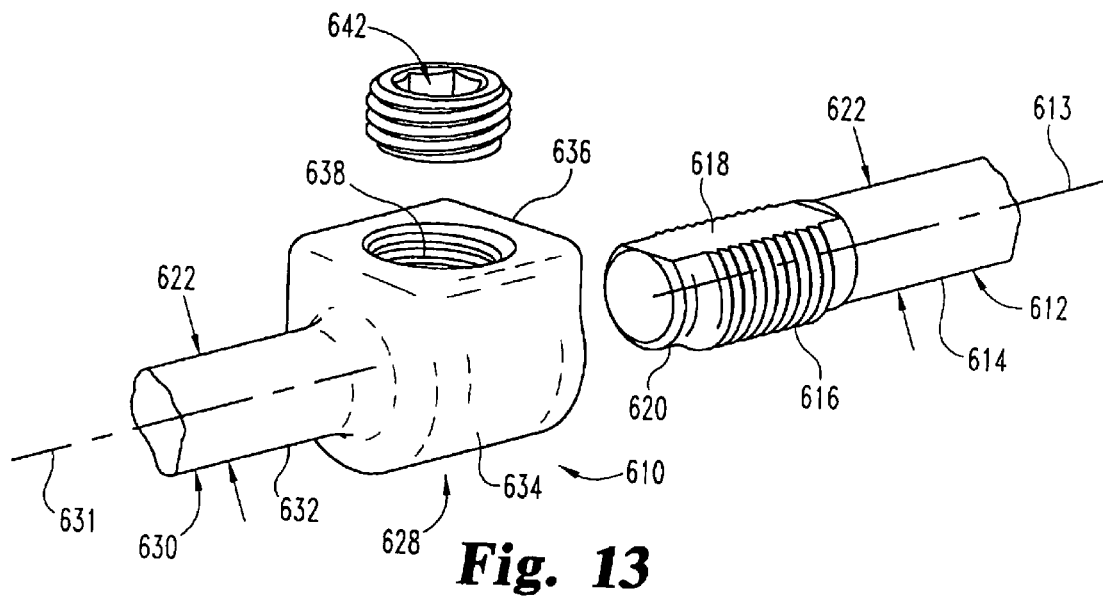
FIG. 13 is an exploded perspective view of a portion of another spinal construct system.
Figure 14:
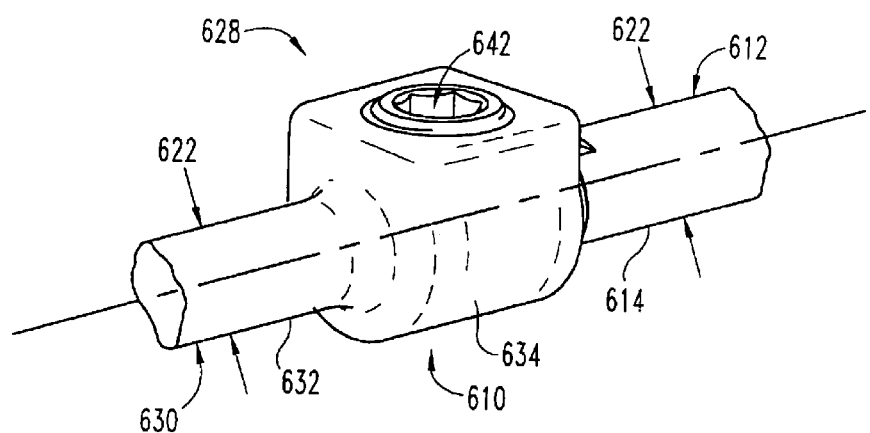
FIG. 14 is an assembled perspective view of the spinal construct system of FIG. 13.

FIGS. 13-14 shown another embodiment connection assembly 610 similar to the embodiment shown in FIGS. 1-2, except for rods 612, 630 having the same cross-sectional dimension 622 transversely to longitudinal axes 613, 631. Rods 612, 630 are coupled to one another in end-to-end fashion with longitudinal axis 613, 631 aligned with one another. Rod 612 includes a rod portion 614, a coupling member 616 having external threads, a contact portion 618 along coupling member 616, and an end member 620. Rod 630 includes a rod portion 632 providing a coupling mechanism 628 having a coupling body 634 integrally formed with rod portion 632. Coupling body 634 includes an axial bore to threadingly receive coupling member 616. Engaging member 642 is threadingly received in trans-axial bore 638 to engage rod 612 at contact surface 618 and prevent it from rotating in coupling body 634.

Figure 15:
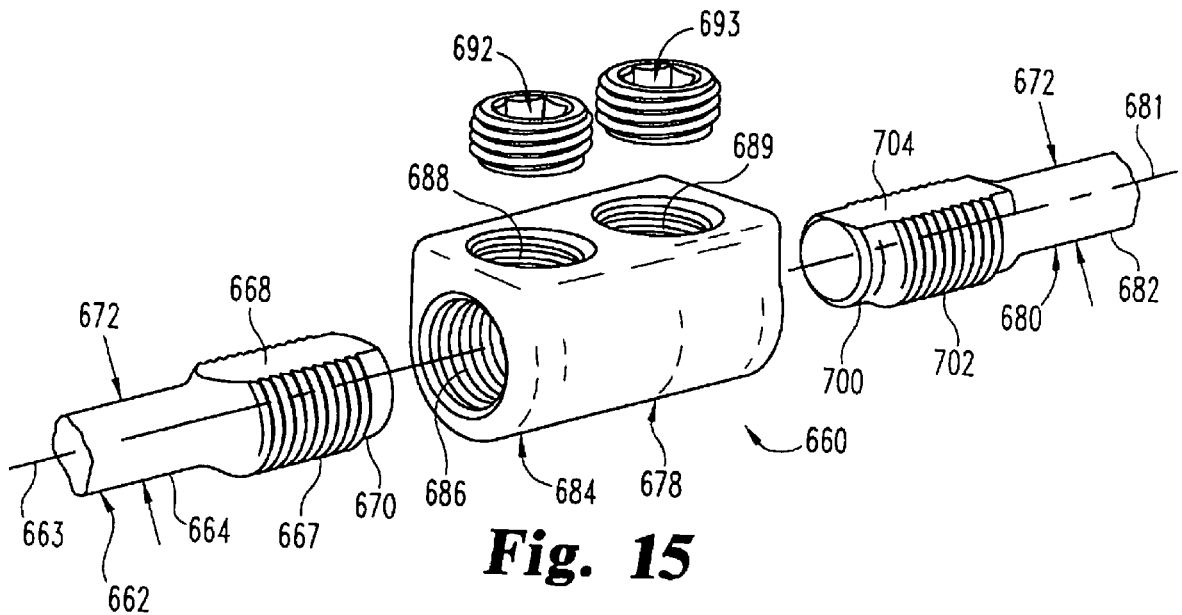
FIG. 15 is an exploded perspective view of a portion of another spinal construct system.
Figure 16:
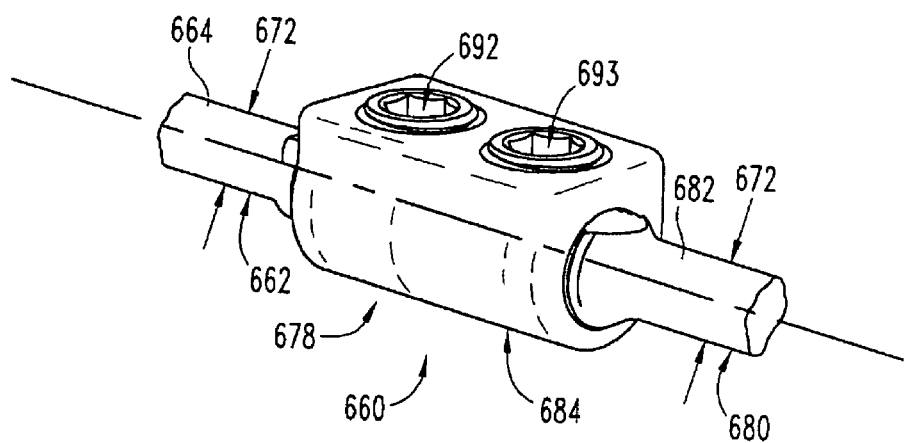
FIG. 16 is an assembled perspective view of the spinal construct system of FIG. 15.

FIGS. 15-16 shown another embodiment rod connection assembly 660 similar to the embodiment shown in FIGS. 9-10, except for rods 662, 680 having the same cross-sectional dimension 672 transversely to longitudinal axes 663, 681. Rods 662, 680 are coupled to one another in end-to-end fashion with longitudinal axis 663, 681 aligned with one another. Rod 662 includes a rod portion 664, a coupling member 667 having external threads, a contact portion 668 along coupling member 667, and an end member 670. Similarly, rod 680 includes a rod portion 682, a coupling member 702 having external threads, a contact portion 704 along coupling member 702, and an end member 700. A coupling mechanism 678 includes coupling body 684 with an axial passage 686 to threadingly engage coupling members 667, 702 in end-to-end fashion with axis 663, 681 aligned with one another. Engaging members 692, 693 are threadingly received in respective ones of trans-axial bores 688, 689 to engage the respective coupling members 667, 702 and prevent rotation of rods 662, 680 in coupling body 684.

Figure 17:
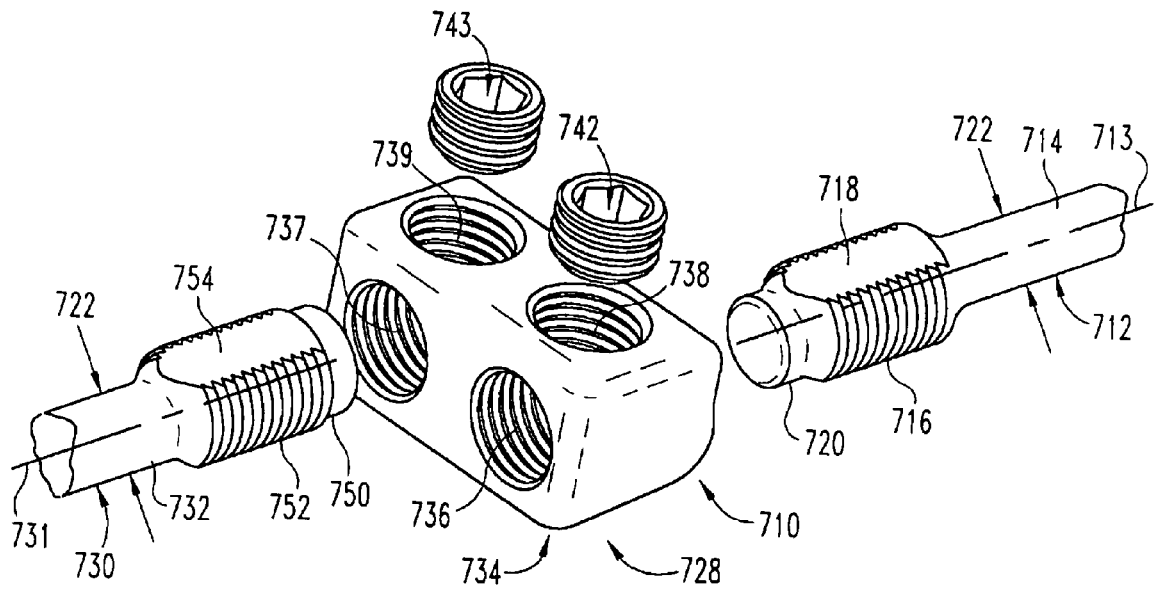
FIG. 17 is an exploded perspective view of a portion of another spinal construct system.
Figure 18:
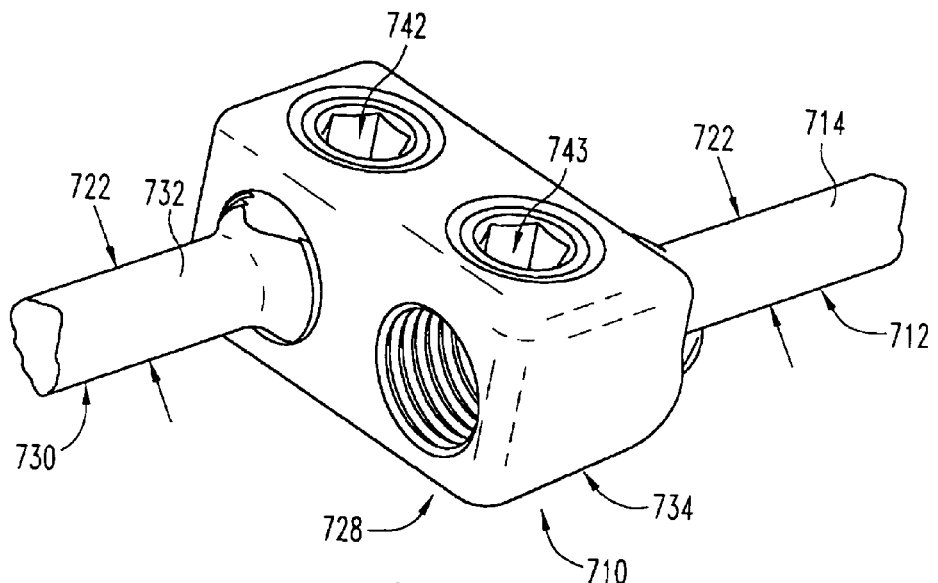
FIG. 18 is an assembled perspective view of the spinal construct system of FIG. 17.

FIGS. 17-18 shown another embodiment rod connection assembly 710 similar to the embodiment shown in FIGS. 11-12, except for rods 712, 730 having the same cross-sectional dimension 722 transversely to longitudinal axes 713, 731. Rods 712, 730 are coupled to one another in end-to-end fashion with longitudinal axis 713, 731 laterally offset from one another. Rod 712 includes a rod portion 714, a coupling member 716 having external threads, a contact portion 718 along coupling member 716, and an end member 720. Similarly, rod 730 includes a rod portion 732, a coupling member 752 having external threads, a contact portion 754 along coupling member 752, and an end member 750. A coupling mechanism 728 includes coupling body 734 with axial passages 736, 737 to threadingly engage coupling members 716, 752 in end-to-end fashion with axes 713, 731 offset laterally relative to one another. Engaging members 742, 743 are threadingly received in respective ones of trans-axial bores 738, 739 to engage the respective coupling members 716, 752 at contact surfaces 718, 754 and prevent rotation of rods 712, 730 in coupling body 734.

Figure 19:
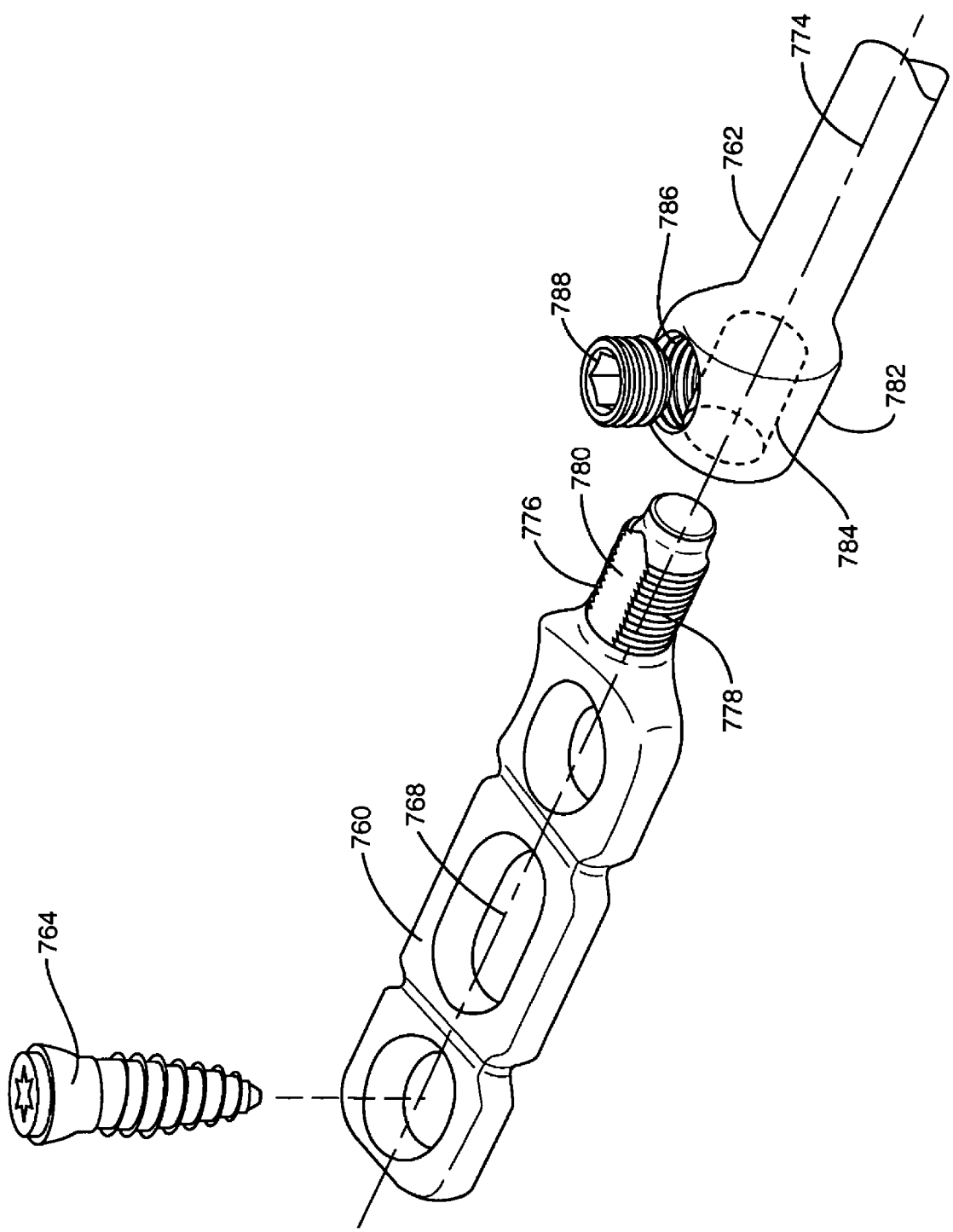
FIG. 19 is an exploded perspective view of one embodiment of a spinal construct system.

FIG. 19 illustrates another embodiment of the spinal construct system having a spinal fixation plate 760 coupled to a fixture element 762 in end-to-end fashion. The spinal fixation plate 760 may include at least one bore 768 sized to accept a bone anchoring component 764. A male coupling member 776 extends outward from an edge of the plate 760. The male coupling member 776 comprises an externally threaded surface 778 and a non-threaded contact surface 780 along at least one side thereof. As described above, the contact surface may be substantially flattened.

The fixture element 762 includes a female coupling body 782 having a first bore 784 that receives the male coupling member 776. The first bore 784 may be internally threaded to engage the externally threaded surface 778 of the male coupling member 776. This connection resists axial displacement of the spinal fixation plate 760 relative to the fixture element 762. The female coupling body 782 further has a second bore 786 extending through the coupling body 782 transverse to the first bore 784 and in communication with the first bore 784. An engagment member 788 is disposed in the second bore 786 and engages the contact surface 780 so as to resist relative rotation between the spinal fixation plate 760 and the fixture element 762. The second bore 786 may be internally threaded and the engagement member 788 may be externally threaded for threaded engagement in the second bore.

Figures 20A, 20B:
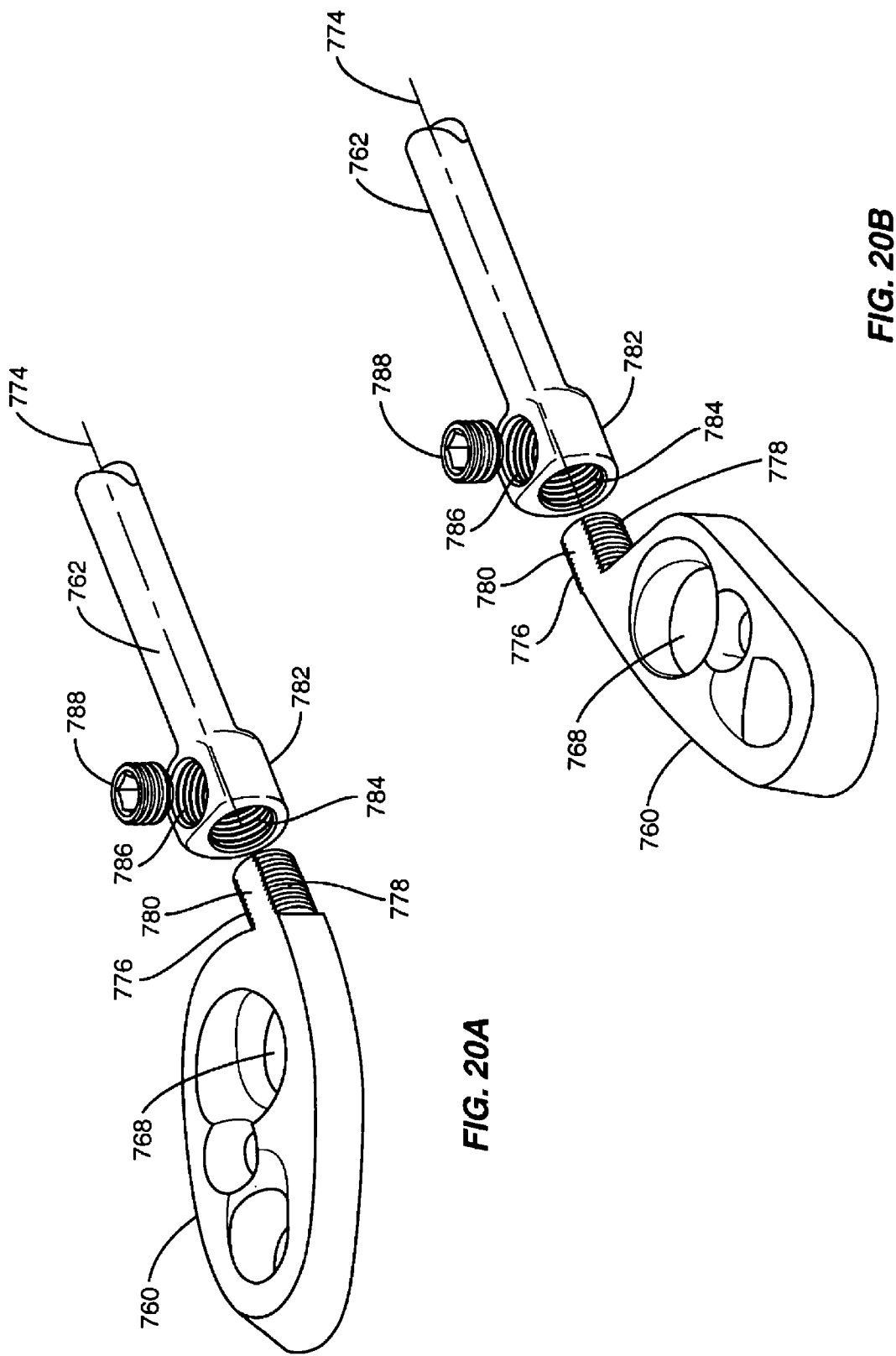
FIG. 20 is an exploded perspective view of one embodiment of a spinal construct system.

The spinal fixation plate 760 and the fixture element 762 illustrated in the embodiment of FIG. 19 are axially aligned about a common longitudinal axis. In another embodiment, the two elements may be laterally offset about a common longitudinal axis, similar to the embodiments illustrated in FIGS. 17 and 18. FIGS. 20A and 20B illustrate embodiments having a longitudinal axis of the plate 760 offset from an axis of the fixture element 762.

The embodiments of FIG. 19, 20A, and 20B each include the female coupling body 782 associated with the fixture element 762. In other embodiments, the female coupling body 782 may be associated with the spinal fixation plate 760.

Figure 21:
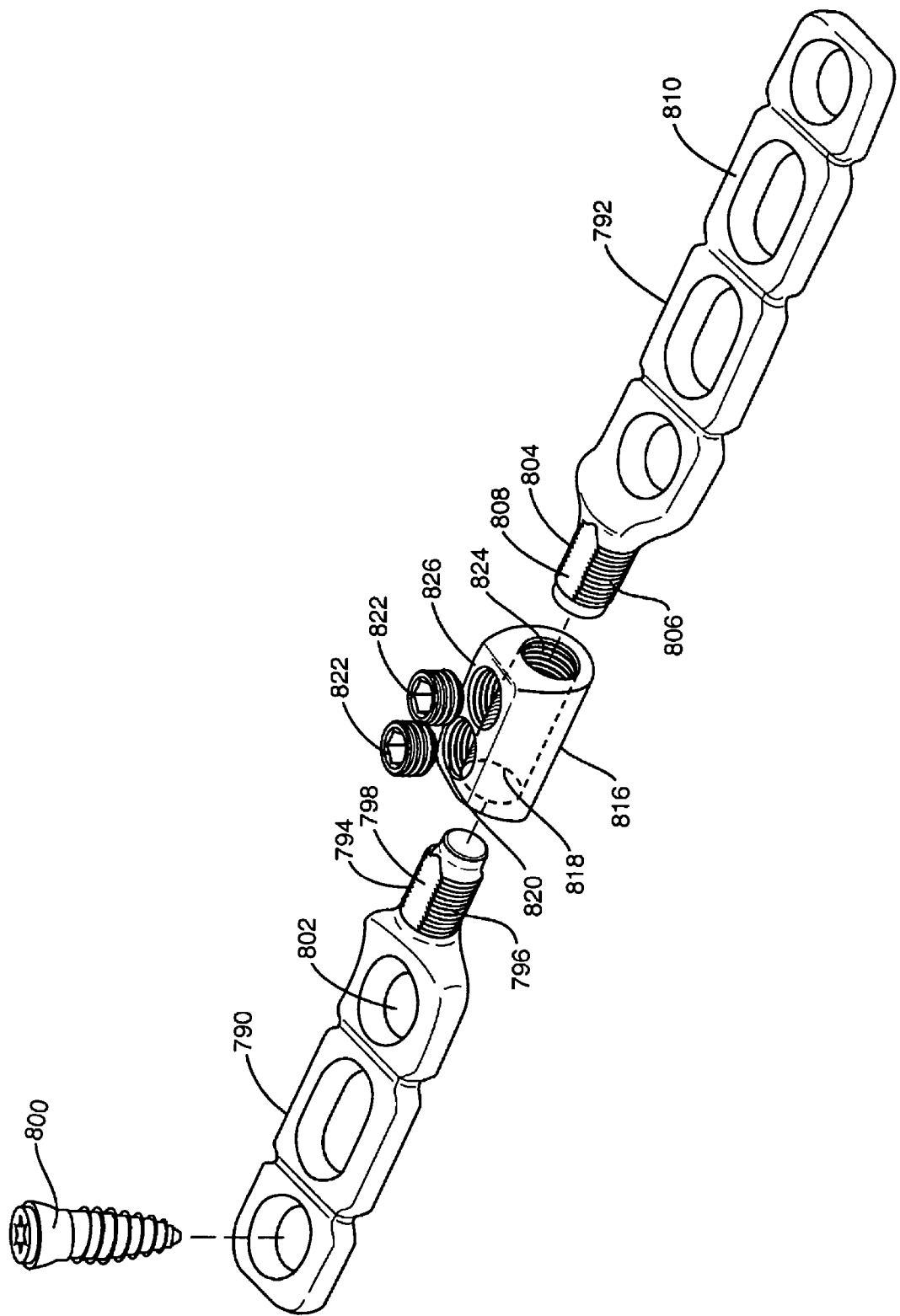
FIG. 21 is an exploded perspective view of one embodiment of a spinal construct system.
Figure 22:
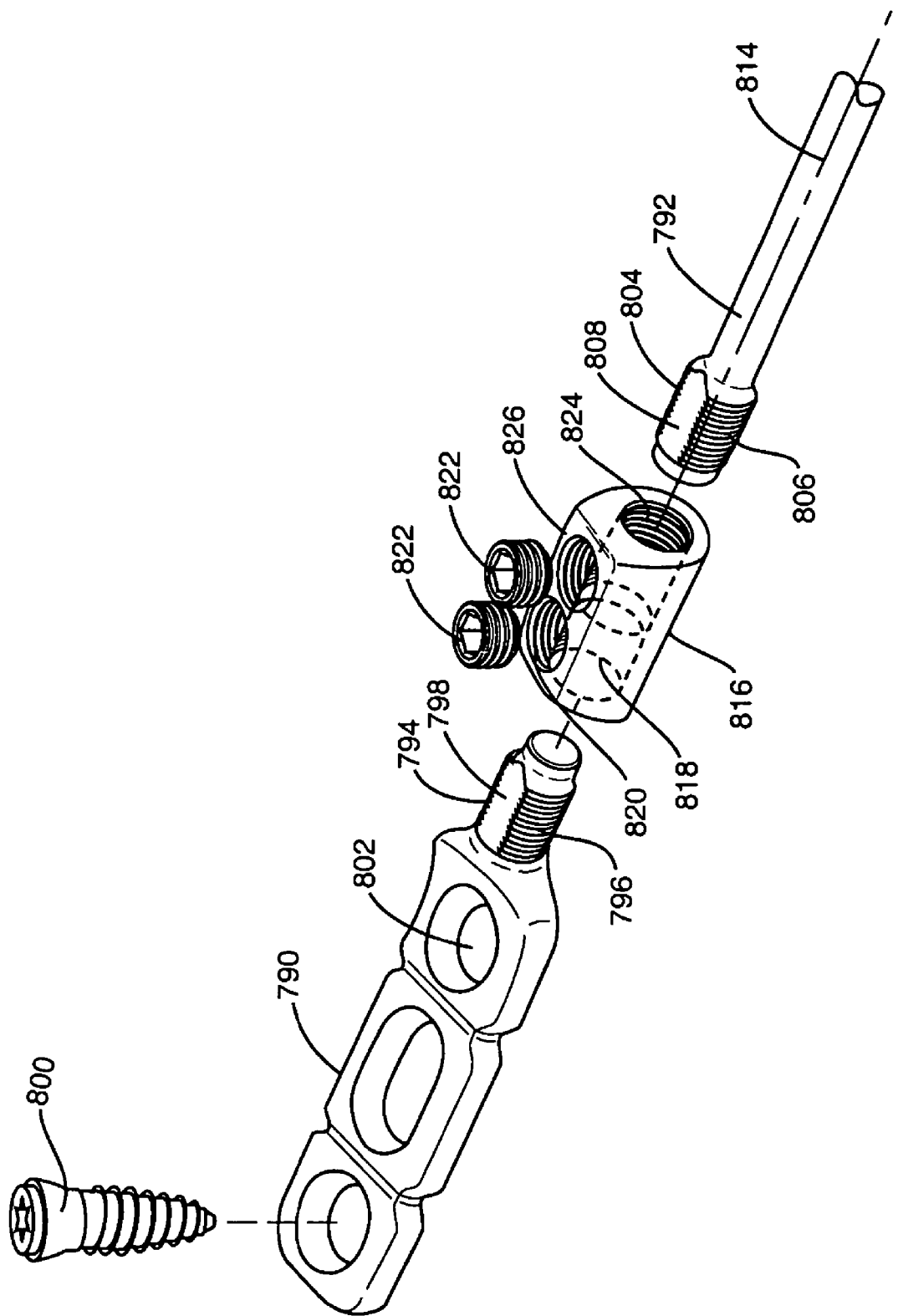
FIG. 22 is an exploded perspective view of one embodiment of a spinal construct system.
Figure 23:
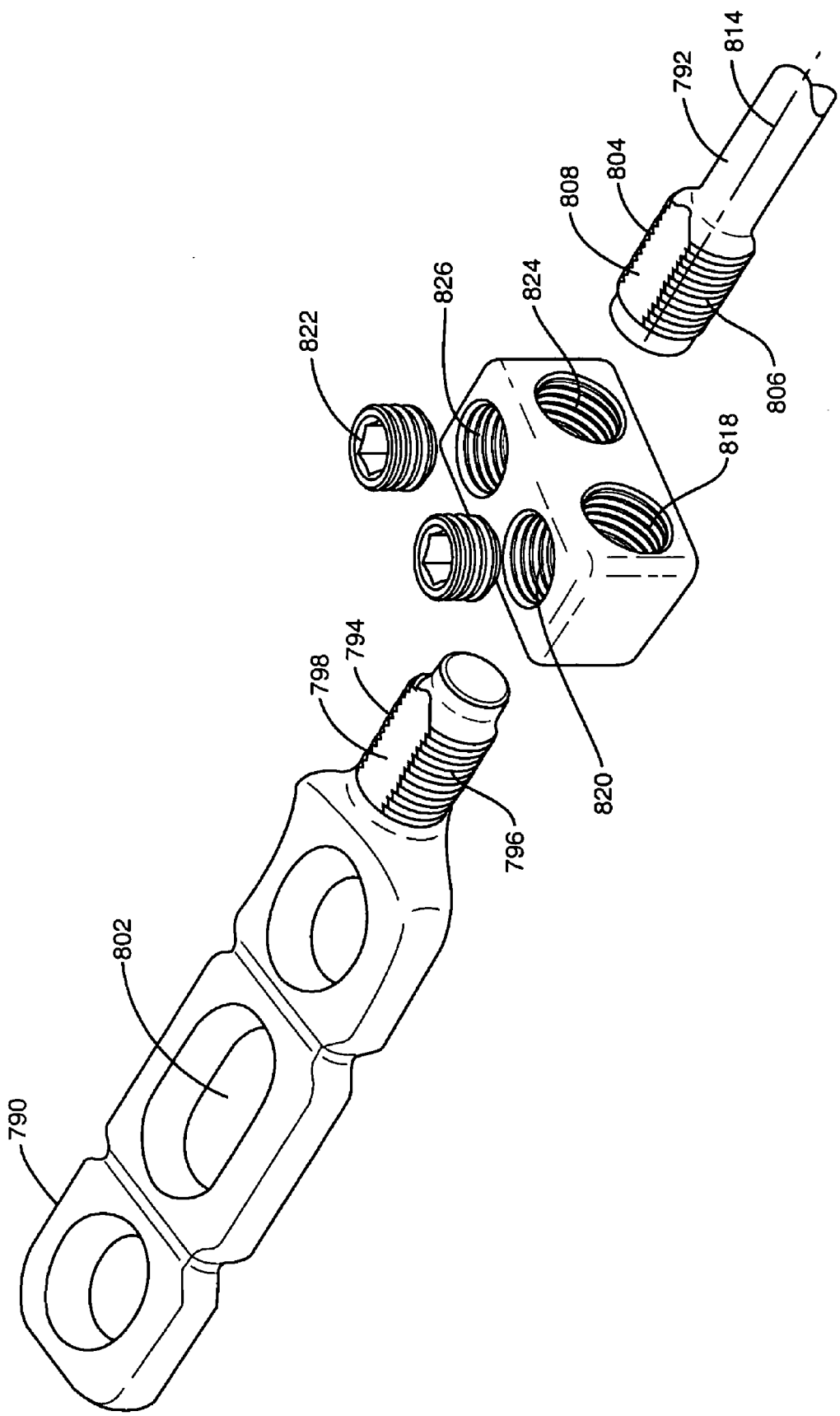
FIG. 23 is an exploded perspective view of one embodiment of a spinal construct system.

FIG. 21-23 illustrate embodiments having a coupling body 816 that couples spinal fixation plate 790 to fixture element 792. The spinal fixation plate 790 has a first male coupling member 794 extending from an edge thereof. The first male coupling member 794 comprises a first externally threaded surface 796 and a first non-threaded contact surface 798 along at least one side thereof. The spinal fixation plate 790 may, as appropriate, include one or more bone anchoring components 800 or transverse bore(s) 802 for accepting bone anchoring components 800.

The fixture element 792 may have a second male coupling member 804 extending from a first end thereof. The second male coupling member 804 comprises a second externally threaded surface 806 and a second non-threaded contact surface 808 along at least one side thereof. Embodiments of the fixture element 792 comprise a second spinal fixation plate 810 (FIG. 21), an aligned elongated rod 814 (FIG. 22), or an offset elongated rod (FIG. 23).

A female coupling body 816 couples the spinal fixation plate 790 to the fixture element 792 in end-to-end fashion so as to resist axial displacement of said spinal fixation plate 790 relative to the fixture element 792. The female coupling body 816 has a first bore 818 that receives the first male coupling member 794. The female coupling body 816 has a second bore 820 extending transverse to the first bore 818 and in communication with the first bore 818. The second bore 820 may be internally threaded and the engagement member 822 may be externally threaded for threaded engagement in the second bore 820. An engagement member 822 contacts the first contact surface 798 so as to resist relative rotation between the spinal fixation plate 790 and the fixture element 792.

A third bore 824 is also included in the female coupling body 816 to receive the second male coupling member 804. The female coupling body 816 may advantageously also include a fourth bore 826 transverse to the third bore 824 and in communication with the third bore 824. A second engagement member 822 is disposed in the fourth bore 826 to contact the second contact surface 808 so as to resist relative rotation between the fixture element 792 and the spinal fixation plate 790. The third bore 824 may be parallel, aligned, or offset to the first bore 818 so that the spinal fixation plate 790 and the fixture element 792 may be axially aligned about a common longitudinal axis or laterally offset about a common longitudinal axis, as is desired.

In the embodiments illustrated in FIGS. 19-24, the male members comprise exterior threaded surfaces that engage with corresponding threaded surfaces of the female member. In another embodiment, the members are not threadingly engaged. The members may be maintained in position by locking elements such as the engagement members, adhesives, or other sources.

In one embodiment, the coupling body 816 includes male members that extend outward from the body and engage with corresponding female members in the elements.

Figure 24:
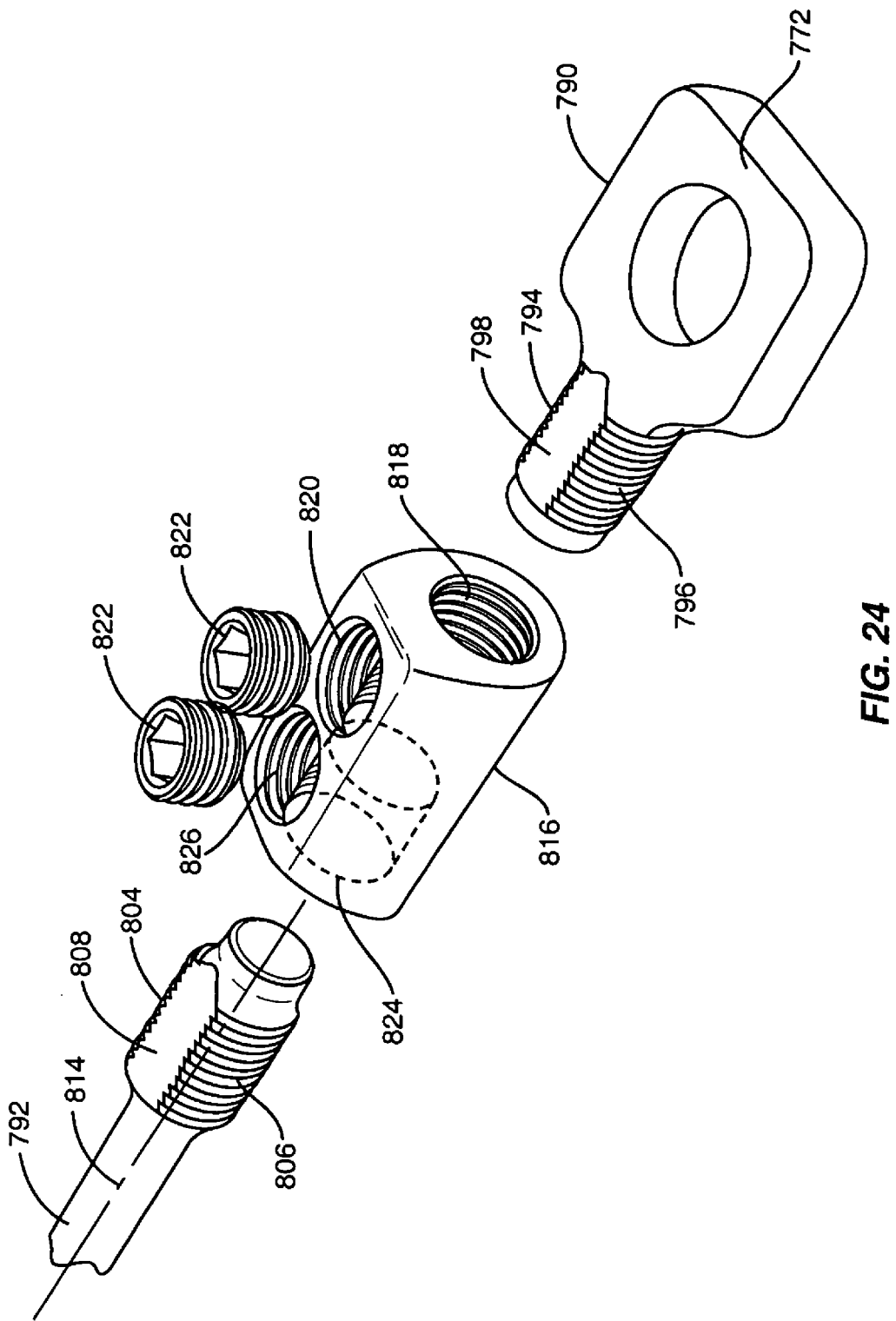
FIG. 24 is an exploded perspective view of one embodiment of a spinal construct system.

In an alternative embodiment, the spinal fixation plate may comprise a spinal fixation block 772 as illustrated in FIG. 24. Such a spinal fixation block 772 may include a transverse bore 768 for accepting a bone anchoring component 764.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A spinal construct system comprising:
   a spinal fixation plate including an elongated flat shape with a lower surface sized to lie against a portion of a spinal column, said plate including a length sized to include at least two transverse bores for receiving bone anchoring elements, said length greater than a width of said plate and a height of said plate less than said width, said height of said plate being less than each of said length and width of said plate;
   a fixture element coupled to said spinal fixation plate in end to end fashion;
   a male coupling member formed integrally with one of said spinal fixation plate and said fixture element, the male coupling member and one of said spinal fixation plate and said fixture element comprising a single unitary body; said male coupling member comprising an externally threaded surface and a non-threaded contact surface along at least one side thereof;
   a female coupling body associated with the other of said spinal fixation plate and said fixture element; said female coupling body comprising a first bore receiving said male coupling member and threadingly engaging said externally threaded surface of said male coupling member so as to resist axial displacement of said spinal fixation plate to said fixture element; said female coupling body further comprising a second bore extending through said female coupling body transverse to said first bore and in communication with said first bore; and
   an engaging member disposed in said second bore and engaging said contact surface so as to resist relative rotation between said spinal fixation plate and said fixture element.

2. The system of claim 1 wherein said spinal fixation plate includes said male coupling member.

3. The system of claim 1 wherein said spinal fixation plate includes three or more transverse bores with at least one of the transverse bores including an oblong shape.

4. The system of claim 1 wherein said fixture element is a second spinal fixation plate.

5. The system of claim 1 wherein said fixture element is a spinal fixation block.

6. The system of claim 1 wherein said contact surface is substantially flattened.

7. The system of claim 1 wherein said spinal fixation plate and said fixture element are axially aligned about a common longitudinal axis.

8. The system of claim 1 wherein said spinal fixation plate and said fixture element are laterally offset about a common longitudinal axis.

9. A spinal construct system comprising:
- a spinal fixation plate having a first male coupling member integrally formed thereon such that the first male coupling member extends from a first end of the spinal fixation plate, said spinal fixation plate including a height between a lower surface and an upper surface of the spinal fixation plate, a midline of said height extending through said first male coupling member, said first male coupling member comprising a first externally threaded surface;
- a fixture element having a second male coupling member extending from a first end thereof, said second male coupling member comprising a second externally threaded surface;
- a female coupling body coupling said spinal fixation plate to said fixture element with the first and second male coupling members oriented in end to end fashion so as to prevent axial displacement of said spinal fixation plate relative to said fixture element; said female coupling body comprising a first bore for receiving said first male coupling member, said female coupling body further comprising a second bore extending through said female coupling body transverse to said first bore and in communication with said first bore, said first bore internally threaded for threaded engagement with said first externally threaded surface of said first male coupling member; and
- an engaging member disposed in said second bore and engaging said first male coupling member so as to resist relative rotation between said spinal fixation plate and said fixture element.

10. The system of claim 9 wherein said fixture element is a second spinal fixation plate.

11. The system of claim 9 wherein said fixture element is a spinal fixation block having a transverse bore.

12. The system of claim 9 wherein said fixture element is an elongated rod.

13. The system of claim 9 wherein said female coupling body includes a third bore for receiving said second male coupling member, said female coupling body further comprising a fourth bore extending through said female coupling body transverse to said third bore and in communication with said third bore.

14. The system of claim 13 wherein said third bore is parallel to said first bore.

15. The system of claim 13 wherein said third bore and said first bore are aligned.

16. The system of claim 13 wherein said third bore and said first bore are offset.

17. The system of claim 9 wherein said spinal fixation plate and said fixture element are axially aligned about a common longitudinal axis.

18. The system of claim 9 wherein said spinal fixation plate and said fixture element are laterally offset about a common longitudinal axis.

19. The system of claim 9, wherein:
- said fixture element is an elongated rod;
- said second bore in said female coupling body is internally threaded and said engagement member is externally threaded for threaded engagement in said second bore;
- said female coupling body includes a third bore for receiving said second male coupling member and threadingly engaging said second externally threaded surface; said female coupling body further comprising a fourth bore extending through said female coupling body transverse to said third bore and in communication with said third bore;
- a second engaging member disposed in said fourth bore and engaging said second male coupling member so as to resist relative rotation between said elongated rod and said spinal fixation plate;
- said third bore is parallel to said first bore.

20. The system of claim 9, wherein the first male coupling member comprises a first non-threaded contact surface along at least one side thereof, and the second male coupling member comprises a second non-threaded contact surface along at least one side thereof.

21. A spinal construct system comprising:
- a spinal fixation plate including an elongated flat shape with a lower surface sized to lie against a portion of a spinal column, said plate including a length sized to include at least two transverse bores for receiving bone anchoring elements, said length greater than a width of said plate and a height of said plate less than said width, said height of said plate being less than each of said length and width of said plate;
- a fixture element coupled to said spinal fixation plate in end to end fashion;
- a male coupling member associated with one of said spinal fixation plate and said fixture element;
- a female coupling body associated with the other of said spinal fixation plate and said fixture element; said female coupling body comprising a first bore receiving said male coupling member so as to resist axial displacement of said spinal fixation plate to said fixture element; said female coupling body further comprising a second bore extending through said coupling body transverse to said first bore and in communication with said first bore; and
- an engaging member disposed in said second bore and engaging said male coupling member so as to resist relative rotation between said spinal fixation plate and said fixture element.

* * * * *